(12) United States Patent
Pearson

(10) Patent No.: US 11,395,881 B2
(45) Date of Patent: Jul. 26, 2022

(54) AUTO-INJECTOR APPARATUS

(71) Applicant: OWEN MUMFORD LTD, Oxfordshire (GB)

(72) Inventor: Lee Pearson, Oxfordshire (GB)

(73) Assignee: Owen Mumford Limited, Oxfordshire (GB)

( * ) Notice: Subject to any disclaimer, the term of this patent is extended or adjusted under 35 U.S.C. 154(b) by 580 days.

(21) Appl. No.: 16/071,293

(22) PCT Filed: Jan. 19, 2017

(86) PCT No.: PCT/GB2017/050115
§ 371 (c)(1),
(2) Date: Jul. 19, 2018

(87) PCT Pub. No.: WO2017/125733
PCT Pub. Date: Jul. 27, 2017

(65) Prior Publication Data
US 2020/0282144 A1 Sep. 10, 2020

(30) Foreign Application Priority Data
Jan. 19, 2016 (GB) ..................... 1600988

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31576* (2013.01); *A61M 5/3202* (2013.01); *A61M 2005/2073* (2013.01)

(58) Field of Classification Search
CPC ............ A61M 5/2033; A61M 5/31576; A61M 2005/2073; A61M 5/326; A61M 5/3243
See application file for complete search history.

(56) References Cited

U.S. PATENT DOCUMENTS

| 5,562,626 A | 10/1996 | Sanpietro |
| 8,038,649 B2 | 10/2011 | Kronestedt |
| 8,932,254 B2 | 1/2015 | Eaton |
| 9,302,054 B2 | 4/2016 | Eaton et al. |
| 9,943,646 B2 | 4/2018 | Holland |

FOREIGN PATENT DOCUMENTS

| CN | 1187102 C | 2/2005 |
| CN | 1630541 A | 6/2005 |
| CN | 105025954 A | 11/2015 |
| GB | 2 463 071 A | 3/2010 |
| GB | 2 529 507 A | 2/2016 |

(Continued)

OTHER PUBLICATIONS

International Search Report, dated Apr. 26, 2017, from corresponding PCT application No. PCT/GB2017/050115.

(Continued)

*Primary Examiner* — Bradley J Osinski
(74) *Attorney, Agent, or Firm* — Quarles & Brady LLP

(57) ABSTRACT

Disclosed is an auto-injector apparatus for receiving a safety syringe, the safety syringe including a sheath deployable on actuation of a plunger to a position at least partially covering a needle of the syringe, wherein the apparatus is configured to allow movement of the sheath to a closed position that substantially covers the needle.

16 Claims, 2 Drawing Sheets

(56) References Cited

FOREIGN PATENT DOCUMENTS

| | | |
|---|---|---|
| WO | 03068297 A1 | 8/2003 |
| WO | 2009/037141 A1 | 3/2009 |
| WO | 2010/125400 A2 | 11/2010 |
| WO | 2011/012849 A1 | 2/2011 |
| WO | 2012/135524 A1 | 10/2012 |

OTHER PUBLICATIONS

Office Action and Search Report, related TW Application No. 106101852, dated May 15, 2020, 16 pages. English translation included.
First Office Action from corresponding Chinese Patent Application No. 200780007174.2, dated Mar. 30, 2020 (18 pages).
Third Office Action from corresponding Chinese Patent Application No. 201780007174.2 dated Aug. 4, 2021 (18 pages) (English translation included).

AUTO-INJECTOR APPARATUS

CROSS-REFERENCE TO RELATED APPLICATIONS

The present application represents the United States National Stage of International Application No. PCT/GB2017/050115, filed on Jan. 19, 2017, which claims priority to British Patent Application Serial No. GB 1600988.8, filed on Jan. 19, 2016, and entitled, "AUTO-INJECTORAPPARATUS," the contents of which are incorporated herein by reference in their entirety.

TECHNICAL FIELD

The invention relates to auto-injector apparatus. In particular embodiments, the invention relates to, but need not be limited to, an auto-injector apparatus for receiving a safety syringe.

BACKGROUND

Safety syringes typically have some form of safety mechanism built into the syringe to protect healthcare workers from accidental needle stick injuries after use. Exemplary safety syringes may include a sheath for covering the needle, or may cause the needle to retract within the barrel of the syringe.

Known safety syringes comprise a spring-loaded safety mechanism that may be engaged by the healthcare worker after the inward stroke of a plunger of the syringe. The spring urges a surface against the skin of the patient, thereby extracting the needle and simultaneously engaging the safety mechanism. Such devices are prone to misuse as the spring-loaded mechanism may cause discomfort and bruising to patients when it is activated. Therefore, healthcare workers are known to remove the needle from the patient before engaging the safety mechanism. This exposes the healthcare worker to the needle after use and the spring-loaded action of the safety mechanism may lead to blood splatter from the needle.

Auto injectors provide a premeasured dose of a particular medication to a patient. By design, auto injectors do not typically require medications to be drawn up via a conventional syringe and so may be used without formal medical training. This is of great significance in high-stress situations, for example during an anaphylactic attack, or for users who may find assembling a traditional syringe difficult. In addition, auto injectors are often used for mass vaccinations by trained medical staff where lengthy conventional syringe use can result in fatigue for the caregiver.

Auto injectors typically comprise a prefilled delivery system such as a syringe or cartridge and a spring-loaded plunger that upon the release moves the prefilled delivery system to its end position, at which point the needle pierces through the tissue. The plunger is also moved to its end position, and the position of the end stop determines the volume of medication ejected.

SUMMARY

According to an aspect of the invention, there is provided an auto-injector apparatus for receiving a safety syringe, the safety syringe comprising a sheath deployable on actuation of a plunger to a position at least partially covering a needle of the syringe, wherein the apparatus is configured to allow movement of the sheath to a closed position that substantially covers the needle.

Optionally, the auto-injector apparatus further comprises a biasing means configured to actuate the plunger.

Optionally, the sheath is configured such that a force applied by the biasing means to the plunger also deploys the sheath.

Optionally, the biasing means comprises one of a compression spring and a rotary spring.

Optionally, the auto-injector apparatus further comprises a biasing means retainer configured to prevent the biasing member from applying a force to the plunger.

Optionally, the auto-injector apparatus further comprises a trigger configured to release the biasing member such that it applies a force for actuation of the plunger.

Optionally, the auto-injector apparatus further comprises a syringe housing configured to receive the safety syringe.

Optionally, the syringe housing comprises a needle aperture through which the needle of the safety syringe projects when the safety syringe is received within the syringe housing.

Optionally, the needle aperture is configured to allow a rigid needle shield fitted to the safety syringe to project from the syringe housing.

Optionally, the auto-injector apparatus further comprises an end cap removably attached to the syringe housing and configured to cover the needle of the syringe.

Optionally, the end cap is configured such that the rigid needle shield is removed from the safety syringe when the housing cap is removed.

Optionally, the needle aperture forms an annular aperture around the needle and is configured to allow the sheath to project from the syringe housing in the closed position.

Optionally, the auto-injector apparatus further comprises a locking mechanism configured to lock the sheath in the closed position.

Optionally, the auto-injector apparatus further comprises a plunger housing configured to receive the plunger of the safety syringe.

Optionally, the plunger housing is removably connected to the syringe housing.

Optionally, the biasing means is within the plunger housing.

Optionally, the auto-injector apparatus further comprises a safety syringe.

Optionally, the safety syringe comprises: a safety plunger, wherein the sheath is deployable on actuation of the safety plunger, and wherein the safety plunger is coupled to a syringe plunger such that an inward stroke of the safety plunger causes the syringe plunger to move within a barrel of the syringe, wherein the safety plunger is configured to decouple from the syringe plunger at a point on the inward stroke such that the safety plunger is moveable independently of the syringe plunger, and wherein further movement of the safety plunger after the first and second points on the inward stroke causes the sheath at least partially to cover the opening in the barrel.

Optionally, the plunger is configured to couple to the sheath at a further point on the inward stroke.

Optionally, the safety syringe further comprises a decoupling mechanism configured to decouple the safety plunger and the syringe plunger.

Optionally, the decoupling mechanism is configured to decouple the safety plunger and the syringe plunger under rotation of the syringe plunger relative to the safety plunger.

Optionally, the decoupling mechanism is configured to decouple the safety plunger and the syringe plunger by way of the force applied to the safety plunger on its inward stroke.

Optionally, the decoupling mechanism comprises: a threaded portion of the safety plunger configured to cooperate with the syringe plunger to exert a rotational force on the syringe plunger on application of a linear force to the safety plunger, wherein the syringe plunger is configured to prevent rotation thereof before the point on the inward stroke and to allow rotation thereof after the point on the inward stroke.

Optionally, the syringe plunger is configured to pass through an aperture, a first portion of the syringe plunger having a cross sectional shape to prevent rotation thereof within the aperture, and a second portion of the syringe plunger having cross sectional shape to allow rotation thereof within the aperture.

Optionally, the threaded portion of the safety plunger comprises a threaded rod configured to cooperate with a correspondingly threaded aperture in the syringe plunger.

According to another aspect of the invention, there is provided a kit of parts comprising: an auto-injector apparatus according to any preceding claim; and a prefilled safety syringe.

DETAILED DESCRIPTION

Generally disclosed herein are auto-injector apparatus for receiving a safety syringe. Exemplary auto-injector apparatus are configured to allow a sheath of the safety syringe to extend from a housing to cover, at least partially, a needle of the safety syringe.

Figure 1:
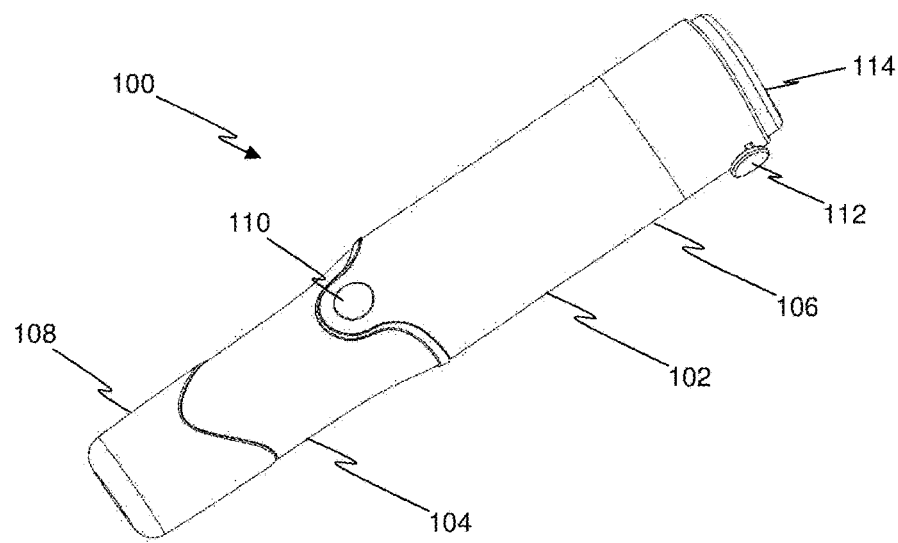
FIG. 1 is a perspective view of an auto-injector apparatus.

Referring to FIG. 1, an auto-injector apparatus 100 comprises an elongated generally tubular body 102 comprising a syringe housing 104 removably connected to a plunger housing 106. Additionally, an end cap 108 may be removably connected to an end of the syringe housing 104. In exemplary apparatus, the end cap 108 may be connected to the syringe housing 104 to cover a needle of a syringe housed within the syringe housing 104.

As used herein, exemplary apparatus may be considered to include a needle end and a plunger end.

Figure 2:
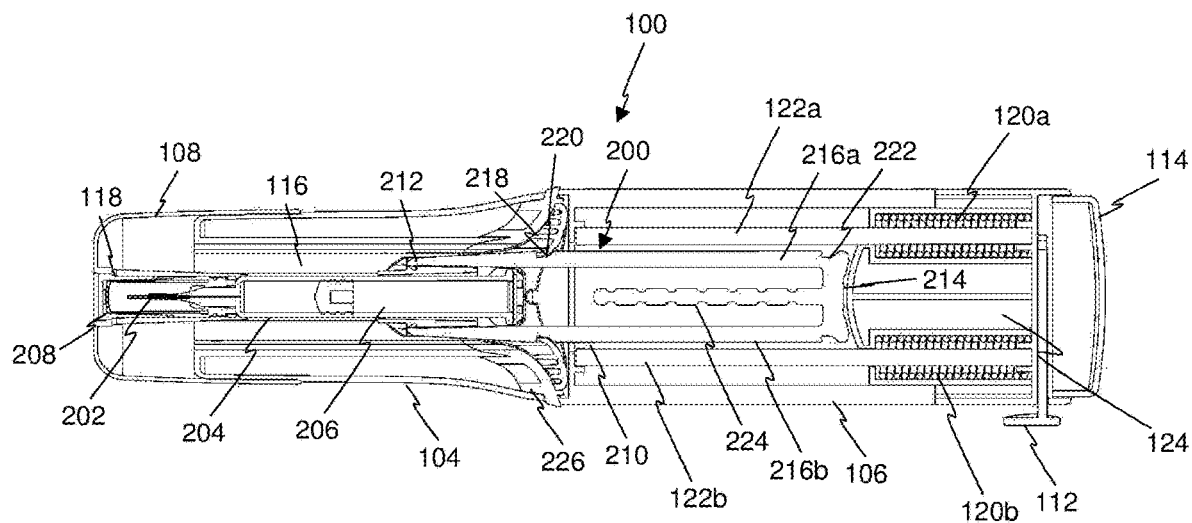
FIG. 2 is a longitudinal cross section through an auto-injector apparatus.

The syringe housing 104 is configured to receive a safety syringe (as shown in FIG. 2) and comprises a generally tubular body that is flared towards the plunger housing 106.

As will be explained later, the needle end of the syringe housing 104 further comprises a needle aperture through which the needle and optionally a rigid needle shield (RNS) project when the safety syringe is received within the syringe housing 104. As also explained later, the syringe housing 104 may also comprise a sheath aperture around the needle aperture configured to allow a sheath to project from the syringe housing 104 to cover at least partially the needle. It is noted that in exemplary apparatus, the sheath aperture may be annular although other shapes are possible. In other exemplary apparatus, the needle aperture may be oversized, such that there is a gap between the wall of the aperture and the wall of a barrel of a syringe within the apparatus. The gap may be sufficient to allow the sheath to pass through the aperture into a position at least partially covering the needle.

The syringe housing 104 is removably connected to the plunger housing 106. The plunger housing 106 may be removably connected to the syringe housing 104 by cooperating features that may be any conventional cooperating features known in the art, such as detents, hooks and undercuts, to removably connect the plunger housing 106 and syringe housing 104 together, for example by a snap fit. A housing release means 110, which is a button in the apparatus of FIG. 1, may be configured to disconnect the syringe housing 104 and the plunger housing 106. That is, when the housing release button 110 is depressed then the syringe housing 104 and plunger housing 106 may be separated.

The plunger housing 106 comprises a plunger activation means 112, which is an activation button in the apparatus of FIG. 1 and a trigger 114, which is a trigger button in the apparatus of FIG. 1. The activation button 112 is configured to make a plunger depression mechanism operable. The trigger is configured to operate the plunger depression mechanism. In exemplary apparatus, the activation button 112 must be depressed in order for the trigger button 114 to be able to operate the plunger depression mechanism.

Referring to FIG. 2, a safety syringe 200 is positioned within the syringe housing 104 of the apparatus 100. The safety syringe 200 comprises a hypodermic needle 202 fixed to an end of a barrel 204. The hypodermic needle 202 is hollow. The barrel 204 comprises an opening at the point where the needle 202 is fixed to it such that a fluid path exists between the barrel 204 and the hollow channel of the needle 202.

A syringe plunger 206 is positioned inside the barrel 204 and is configured to move therein. The syringe plunger 206 may move on an inward stroke wherein the syringe plunger 206 moves further into the barrel 204. The syringe plunger 206 is configured such that the inward stroke causes a substance held in the barrel 204 to be expelled from the open end of the barrel 204 and through the needle 202.

The needle 202 may be any type suitable for the task to be undertaken by the user, such as injecting a drug into a patient. In exemplary safety syringes 200, the needle 202 is fixedly attached to the open end of the barrel 204. In other exemplary safety syringes 206, the needle 202 may be removably attached to the barrel 204. In such safety syringes 200, the needle 202 may be replaced by other needles of the same or a different type.

In the exemplary apparatus of FIG. 2, the safety syringe further comprises a rigid needle shield 208 (RNS) consisting of a hollow substantially tubular configuration with a closed end and an open end configured to be positioned to cover the needle 202. RNS are typically comprised of a compliant elastomeric needle shield such as rubber and a generally rigid shell such as polypropylene. RNS are known in the art.

In the exemplary apparatus of FIG. 2, a safety plunger 210 is coupled to a sheath 212 and comprises a head 214 and arms 216a, 216b connecting the head 214 to the sheath 212. The arms 216a, 216b are moveable along the outside of the barrel 204 such that the sheath 212 moves along the outside of the barrel 204 on application of a force to the head 214.

The sheath 212 may be at least partially received within the syringe housing 104 when the syringe plunger 210 is at the outermost part of its stroke.

The apparatus comprises a locking mechanism configured to lock the sheath 212 in the closed position, that is, when it is at least partially covering the needle 202.

As shown in FIG. 2, the locking mechanism of the exemplary apparatus comprises a sheath latch 218. The sheath latch may form part of a handle portion (described below) of a safety syringe, or may form part of the apparatus 100 itself. The sheath latch 218 is configured to engage with a first sheath retaining recess 220 when the sheath 212 is in an open position and the safety plunger 210 is extended. The sheath latch 218 is further configured to engage with a second sheath retaining recess 222 when the sheath 212 is in a closed position and the safety plunger 210 is at the end of its inward stroke.

In exemplary apparatus, the first and second sheath retaining recesses 220, 222 form part of the arms 216a, 216b of the safety plunger 210. Further, there may be a set of a sheath latch 218 and first and second sheath retaining recesses 220, 222 for each arm 216a, 216b.

The safety plunger 210 be coupled to the syringe plunger 206 at a first point on an inward stroke of the safety plunger 210 and may be decoupled from the syringe plunger 206 at a second point on the inward stroke. The safety plunger 210 may be coupled to the syringe plunger 206 by a coupling portion 224 configured to ensure that the syringe plunger 206 and the safety plunger 210 move together when the coupling member 224 is in contact with the syringe plunger 206.

As used herein, the term "coupled" encompasses a situation where there is corresponding linear movement of two coupled features. Coupled features may move in the same direction. Conversely, the term "decoupled" encompasses a situation where there is independent movement between decoupled features. In exemplary apparatus, a feature that is decoupled from another feature may be configured to move while the other feature remains stationary. In other exemplary apparatus, a feature that is decoupled from another feature may be configured to move linearly while the other feature moves rotationally.

The coupling portion 224 may be a threaded rod configured to be received within the syringe plunger 206. The syringe plunger 206 may comprise an internal thread corresponding to the threaded rod 224. The syringe plunger 206 may be configured such that it is not rotatable. Therefore, when the threaded rod 224 is received within the syringe plunger 206, the safety plunger 210 and the syringe plunger 206 are coupled. The threaded rod 224 exerts a rotational force on the syringe plunger 206, but the syringe plunger 206 is not rotatable and so there is linear movement of the syringe plunger 206 with linear movement of the safety plunger 210.

The syringe plunger 206 may be prevented from rotating by a keyed aperture that the syringe plunger 206 passes through and a corresponding cross sectional shape of the syringe plunger 206.

A top section of the syringe plunger 206 may have a cross sectional shape that is able to rotate within the keyed aperture. Therefore, as the syringe plunger moves to a point on the inward stroke where the top section of the syringe plunger 206 is aligned with the keyed aperture, the rotational force applied by the threaded rod 224 is able to rotate the syringe plunger 206 and the syringe plunger 206 and the safety plunger 210 become decoupled.

The syringe housing 104 is configured to receive a handle portion 226 of the safety plunger 200 such that the safety plunger 200 is fixed with respect to the syringe housing 104. The barrel 204 extends into a chamber 116 within the syringe housing 104. The chamber 116 has a width greater than a diameter of the barrel 204 to allow the sheath 212 to move over the barrel 204 within the chamber 116. The chamber 116 may have a circular cross section, although other shaped cross sections are possible. The chamber 116 is open at one end.

In exemplary apparatus, the needle 202 may extend from the open end of the chamber 116. The open end of the chamber 116 forms an annular aperture around the barrel 204 for allowing the sheath 212 to pass through the chamber 116 to extend from the open end to at least partially cover the needle 202.

The end cap 108 is configured to be removably fitted to a needle end of the syringe housing 104. The end cap 108 comprises an RNS receiver 118 that is configured to fit over an RNS 208 fitted to the syringe 200 when the end cap 108 is placed on the syringe housing 104. The RNS receiver 118 comprises sidewalls configured to fit around the RNS 208 and to couple to the RNS 208 such that removal of the end cap 108 results in removal of the RNS 208.

The end cap 108 substantially covers the needle 202 of the syringe and RNS 208 and is adapted to remove the RNS 118 from the safety syringe 200 when the end cap 108 is removed from the syringe housing 104. In exemplary auto-injection apparatus, the RNS receiver 118 comprises cooperative features 302 configured to attach to the RNS 118 during fitting of the end cap 108, for example by a fit between the elastomeric material of the RNS 208 and cooperative features of the end cap 108. The cooperating features can be any conventional cooperating features known in the art, such as snap fits or detents, hooks and undercuts for coupling the RNS 208 within the RNS receiver 118 of the end cap 108.

Typically, auto-injector apparatus require two protective caps. Firstly a rigid needle shield (RNS) and secondly an end cap. A common disadvantage inherent with such auto-injector apparatus is the need for the extra operational step of detaching the RNS after removal of the end cap. Additional operational steps increase the risk of misuse of an auto-injector apparatus because users have to undertake the correct operational sequence at a time of high stress and urgency.

The auto-injection apparatus 100 comprises a plunger depression mechanism configured to depress the safety plunger 210 on activation of the auto-injector apparatus 100. The plunger depression mechanism comprises a biasing means configured to apply a force to the safety plunger 210 for depressing the safety plunger 210 and moving it on its inward stroke. The biasing means may comprise one or more springs. In the exemplary apparatus of FIG. 2, the biasing means comprises a plurality of, and in the exemplary apparatus two, compression springs 120a, 120b placed around guide rods 122a, 122b running longitudinally within the plunger housing 106.

The plunger depression mechanism further comprises a driver carriage 124. The driver carriage 124 is slidable within the plunger housing 106. The driver carriage 124 is coupled to the biasing means such that it slides within the plunger housing 106 under force applied by the biasing means. The driver carriage 124 is positioned between the guide rods 122a, 122b and its movement within the plunger housing 106 is guided accordingly.

The compression springs 120a, 120b are held in a compressed state by a biasing means retainer, which in the exemplary apparatus comprises a spring latch. Depression of the plunger activation button 112 while the trigger 114 is depressed releases the spring latch and allows the compression springs 120a, 120b to apply a force to the driver carriage 124 and thereby depress the safety plunger 210.

Many new medications under development require large masses to be injected, for example monoclonal antibodies. In order to inject a large drug mass it is necessary to either increase the injection volume, or increase the concentration of drug in the formulation.

Increasing the injecting volume requires either a high flow rate, which can be painful to a patient; or a long duration of injection, which can be uncomfortable and difficult to maintain injector position.

Increasing the concentration of the drug in the liquid increases the formulation viscosity. A thin needle is required to maintain patient comfort and an increase in viscosity results in an increase of flow resistance. This in turn increases the injection duration.

In either case a high plunger actuation force is required to ensure that a sufficient dose of medication is delivered to the correct tissue compartment because of the resultant higher subcutaneous tissue compression and extrusion force.

The biasing member may comprise a linear actuator or a rotary actuator (explained below). Examples of suitable actuators may be: mechanical, for example a variable or constant force spring or rotary spring; electrical, for example an electric motor or induction motor; or pneumatic or hydraulic, for example a piston.

Injection devices contain typically a glass syringe, which breaks if too much force is used to drive the formulation through the needle. These forces may be inherently limited in the design of syringe through a combination of weaker points in the glass syringe and the high initial actuation forces of the auto-injector biasing member.

Accordingly, the biasing member may be configured to exert a constant or varying dynamic load on the safety plunger 210 for avoiding peak forces beyond the structural limitations of the syringe and allowing an optimum dose rate for viscose fluids.

The biasing member may further comprise a force controller to adjust the load applied to the safety plunger. Examples of a suitable force controller for a mechanical actuator could include a variable force spring or an opposing force mechanism. Other force controllers could be used as are commonly known in the art.

During operation, a user may remove the end cap 108, consequently removing the RNS 208 received within the RNS receiver 118 and exposing the needle 202. The needle 202 may be inserted by a user into a human or animal subject. The activation button 112 is depressed thereby allowing operation of the apparatus by depression of the trigger 114. The user then depresses the trigger, which releases the spring latch, thereby releasing the compression springs 120a, 120b. The compression springs 120a, 120b, which are initially in a compressed state, expand over the guide rods 122a, 122b to exert a driving force on the driver carriage 124. The driver carriage 124 slides within the plunger housing 106 applying a force to the head 214 of the safety plunger 210.

The force applied to the head 214 begins the inward stroke of the safety plunger 210. At a first point on the inward stroke, the safety plunger 210 and the syringe plunger 206 couple. The first point on the inward stroke may be the start of the inward stroke. As the safety plunger 210 and the syringe plunger 206 are coupled, the inward stroke of the syringe plunger 206 begins and the syringe plunger 206 moves within the barrel 204 to expel a substance contained within the barrel 204 from the needle 202. The safety plunger 110 and the syringe plunger 108 move together. Movement of the safety plunger 210 on its inward stroke also moves the sheath 212 towards the needle end of the apparatus 100 as the safety plunger 210 and the sheath 212 are coupled.

At a second point on the inward stroke, the syringe plunger 206 and the safety plunger 210 decouple. The syringe plunger 206 and the safety plunger 210 have moved together under the force applied to the head 214 by the compression springs 220a, 220b and the driver carriage 124 to a point at which the top section of the syringe plunger 206 is aligned with the keyed aperture that the syringe plunger 206 passes through. The keyed aperture may be in the handle portion 226. At this point, rotation of the syringe plunger 206 is possible and the rotational force applied to the syringe plunger 206 by the threaded rod 224 rotates the syringe plunger 206. This allows the safety plunger 210 to continue movement on its inward stroke while the syringe plunger 206 rotates in the barrel 204. As such, the safety plunger 210 and the syringe plunger 206 are decoupled. The point at which the decoupling occurs may be the point at which the syringe plunger 206 has completed its inward stroke. That is, the decoupling may occur at the innermost point of the stroke of the syringe plunger 206. This ensures that all of the substance contained within the barrel 204 has been expelled from the syringe 200 before decoupling. It is noted that in exemplary apparatus, decoupling of the safety plunger 210 from the syringe plunger 206 leads to decoupling of the sheath 212 from the syringe plunger 206, as the sheath forms part of the safety plunger 210.

Continued application of force by the compression springs 120a, 120b to the head 214 leads to continued travel of the safety plunger 210. The sheath 212 continues to move towards the needle end of the apparatus 100 and to pass through the chamber 116 of the syringe housing 104. The sheath 212 then protrudes from the needle end of the syringe housing 104 via the annular aperture to at least partially cover the needle 202.

The end of the sheath 212 extends beyond the tip of the needle 202 such that the needle is not exposed. In this position, the sheath 212 may lock in relation to the barrel 204 and needle 202, such that the needle 202 cannot become exposed. In exemplary apparatus, the safety plunger 210 may become locked to the syringe housing 104. In other exemplary apparatus, the sheath latch 218 may snap into the second sheath retaining recesses 222 to lock the sheath in the extended position.

As set out above, the full inward stroke of the safety plunger 210 fulfils the two actions of dispensing the substance in the barrel 204 and the covering of the needle 202 by the sheath 212. These two actions are completed by the force of the biasing member, which in FIG. 2 is the compression springs 220a, 220b. Moreover, the single action for the user is entirely intuitive, as it is no different from the action required to use a standard auto-injector, that of depressing an activation trigger.

After use of the auto-injector apparatus 100, it may be reset to receive a second safety syringe 200. As such, the auto-injector apparatus 100 is re-usable.

Figure 3:
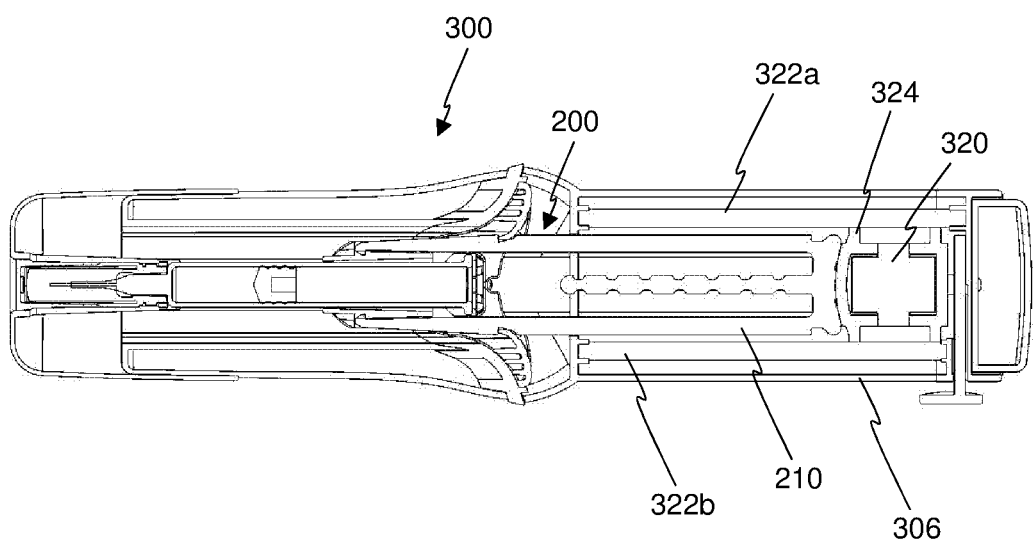
FIG. 3 is a longitudinal cross section through an auto-injector apparatus.

Referring to FIG. 3, a further auto-injector apparatus 300 is shown comprising a safety syringe 200. It is noted that the safety syringe 200 may be the same or similar to the safety syringe described above in relation to FIG. 1. As such, the features of the safety syringe 200 are not described again here. Further, a number of the features of the auto-injector apparatus 300 are the same or similar to those described above in relation to the auto-injector apparatus 100 shown in FIG. 1. Those features are not described again in detail here.

The same or similar features may, where possible, be given similar reference numerals, except prefixed with a "3" rather than a "1".

The biasing member of the auto-injector apparatus 300 may comprise a rotary spring 320. In this exemplary auto-injection apparatus, rotary spring 320 is coupled to a slidable driver carriage 324. In exemplary arrangements, the rotary spring 320 is coupled to the driver carriage 324 in that it may be wound and unwound around a member of the driver carriage 324. A first end of the rotary spring 320 is connected to the driver carriage 324 and a second end of the rotary spring 320 is connected to the plunger housing 306. The second end of the rotary spring 320 is connected to a point on the plunger housing 306 such that the rotary spring 320 is at least partially unfurled or wound when the driver carriage 324 is in a loaded state ready to be activated. That is, there is potential energy stored in the rotary spring 320 when the driver carriage 324 is in a loaded state ready to be activated. When the auto-injection apparatus 300 is operated, the potential energy stored in the rotary spring 320 is released to move the driver carriage 324 and apply a force to depress the safety plunger 210.

The driver carriage 324 cooperates with the head 314 of the safety plunger 210 and is configured to slide along guide rods 322a, 322b. The rotary spring 320 is maintained in an unfurled state in a similar way to that described above in respect of the auto-injector apparatus 100.

The skilled person will envisage further embodiments of the invention without departing from the scope of the appended claims

The invention claimed is:

1. An auto-injector apparatus with a safety syringe received therein, the safety syringe comprising:
    a sheath deployable on actuation of a safety plunger to a closed position substantially covering a needle of the syringe, wherein the auto-injector apparatus is configured to allow movement of the sheath of the safety syringe to said closed position, and
    wherein the auto-injector apparatus comprises:
        a syringe housing configured to receive the safety syringe,
        a chamber configured to allow movement of the sheath of the safety syringe therein, wherein the chamber has a width greater than a diameter of a barrel of the safety syringe to allow the sheath of the safety syringe to move over the barrel within the chamber, and
        a needle aperture through which the needle of the safety syringe projects when the safety syringe is received within the syringe housing, the needle aperture forming an annular aperture around the needle configured to allow the sheath of the safety syringe to project from the syringe housing when in said closed position.

2. An auto-injector apparatus with a safety syringe received therein according to claim 1, further comprising a biasing means configured to actuate the plunger.

3. An auto-injector apparatus with a safety syringe received therein according to claim 2, wherein the sheath is configured such that a force applied by the biasing means to the plunger also deploys the sheath.

4. An auto-injector apparatus with a safety syringe received therein according to claim 2, further comprising a biasing means retainer configured to prevent the biasing member from applying a force to the plunger.

5. An auto-injector apparatus with a safety syringe received therein according to claim 4, further comprising a trigger configured to release the biasing member such that it applies a force for actuation of the plunger.

6. An auto-injector apparatus with a safety syringe received therein according to claim 2, further comprising a plunger housing configured to receive the plunger of the safety syringe, wherein the biasing means is within the plunger housing.

7. An auto-injector apparatus with a safety syringe received therein according to claim 1, further comprising a locking mechanism configured to lock the sheath in the closed position.

8. An auto-injector apparatus with a safety syringe received therein according to claim 1,
    wherein the safety plunger is coupled to a syringe plunger at a first point on an inward stroke of the safety plunger such that the inward stroke of the safety plunger causes the syringe plunger to move within the barrel of the syringe,
    wherein the safety plunger is configured to decouple from the syringe plunger at a second point on the inward stroke such that the safety plunger is moveable independently of the syringe plunger,
    and wherein further movement of the safety plunger after the first and second points on the inward stroke causes the sheath at least partially to cover an opening in the barrel.

9. An auto-injector apparatus with a safety syringe received therein according to claim 8, wherein the safety plunger is configured to couple to the sheath at a third point on the inward stroke of the safety plunger.

10. An auto-injector apparatus with a safety syringe received therein according to claim 8, wherein the safety syringe further comprises a decoupling mechanism configured to decouple the safety plunger and the syringe plunger.

11. An auto-injector apparatus with a safety syringe received therein according to claim 10, wherein the decoupling mechanism is configured to decouple the safety plunger and the syringe plunger under rotation of the syringe plunger relative to the safety plunger.

12. An auto-injector apparatus with a safety syringe received therein according to claim 10, wherein the decoupling mechanism is configured to decouple the safety plunger and the syringe plunger by way of the force applied to the safety plunger on its inward stroke.

13. An auto-injector apparatus with a safety syringe received therein according to claim 10, wherein the decoupling mechanism comprises:
    a threaded portion of the safety plunger configured to cooperate with the syringe plunger to exert a rotational force on the syringe plunger on application of a linear force to the safety plunger,
    wherein the syringe plunger is configured to prevent rotation thereof before the point on the inward stroke and to allow rotation thereof after the point on the inward stroke.

14. An auto-injector apparatus with a safety syringe received therein according to claim 13, wherein the syringe plunger is configured to pass through an aperture, a first portion of the syringe plunger having a cross sectional shape to prevent rotation thereof within the aperture, and a second portion of the syringe plunger having cross sectional shape to allow rotation thereof within the aperture.

15. An auto-injector apparatus with a safety syringe received therein according to claim 13, wherein the threaded portion of the safety plunger comprises a threaded rod configured to cooperate with a correspondingly threaded aperture in the syringe plunger.

16. A kit of parts comprising:
an auto-injector apparatus with a safety syringe received therein according to claim 1; and
wherein the safety syringe is prefilled.

\* \* \* \* \*